(12) United States Patent
Myoung et al.

(10) Patent No.: US 11,484,490 B2
(45) Date of Patent: Nov. 1, 2022

(54) SKIN EXTERNAL COMPOSITION CONTAINING AN EXTRACT OF A FERMENTED PRODUCT OF RED YEAST RICE

(71) Applicant: AMOREPACIFIC CORPORATION, Seoul (KR)

(72) Inventors: Kil Sun Myoung, Yongin-si (KR); Jin Sup Shim, Yongin-si (KR); Jae Young Ko, Yongin-si (KR); Yong Jin Kim, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 239 days.

(21) Appl. No.: 16/878,798

(22) Filed: May 20, 2020

(65) Prior Publication Data

US 2020/0368145 A1    Nov. 26, 2020

(30) Foreign Application Priority Data

May 21, 2019    (KR) .......................... 10-2019-0059578

(51) Int. Cl.
| | |
|---|---|
| A61K 8/9794 | (2017.01) |
| A61K 36/899 | (2006.01) |
| A61Q 19/08 | (2006.01) |
| A61K 8/9728 | (2017.01) |
| A61K 36/064 | (2006.01) |

(52) U.S. Cl.
CPC .......... *A61K 8/9794* (2017.08); *A61K 36/899* (2013.01); *A61K 2236/19* (2013.01); *A61K 2236/33* (2013.01); *A61K 2800/85* (2013.01); *A61Q 19/08* (2013.01)

(58) Field of Classification Search
None
See application file for complete search history.

(56) References Cited

U.S. PATENT DOCUMENTS

2015/0342870 A1\* 12/2015 Choi .................... A61Q 19/007
424/115
2017/0151171 A1\* 6/2017 An ......................... A61Q 19/08

FOREIGN PATENT DOCUMENTS

KR    10-1709734 B1    2/2017

\* cited by examiner

*Primary Examiner* — Kyung S Chang
(74) *Attorney, Agent, or Firm* — Sughrue Mion, PLLC

(57) ABSTRACT

The present disclosure relates to an external-use skin preparation composition containing an extract of a fermented product of Red yeast rice. More particularly, it relates to an external-use skin preparation composition capable of providing excellent antioxidant and anti-aging effects by containing, as an active ingredient, an extract of a fermented product of Red yeast rice, which is obtained by further fermenting Red yeast rice, red rice fermented with *Monascus purpureus*, with yeast.

8 Claims, 2 Drawing Sheets

Specification includes a Sequence Listing.

SEQUENCE LISTING

<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: colla1 forward primer

<400> SEQUENCE: 1
gtcacccacc gaccaagaaa cc                                           22

<210> SEQ ID NO 2
<211> LENGTH: 22
<212> TYPE: DNA
<213> ORGANISM: Artificial Sequence
<220> FEATURE:
<223> OTHER INFORMATION: colla1 reverse primer

<400> SEQUENCE: 2
aagtccaggc tgtccaggga tg                                           22

SKIN EXTERNAL COMPOSITION CONTAINING AN EXTRACT OF A FERMENTED PRODUCT OF RED YEAST RICE

CROSS REFERENCE TO RELATED APPLICATIONS

This application claims the benefit of priority from Korean Patent Application No. 10-2019-0059578 filed with the Korean Intellectual Property Office on May 21, 2019, the entire content of which is hereby incorporated by reference.

TECHNICAL FIELD

One aspect of the present disclosure relates to an external-use skin preparation composition containing an extract of a fermented product of red yeast rice. More particularly, it relates to an external-use skin preparation composition capable of providing excellent antioxidant and anti-aging effects by containing, as an active ingredient, a fermented product of red yeast rice, which is obtained by further fermenting red yeast rice, red rice fermented with *Monascus purpureus*, with yeast.

Background Art

In recent years, with the advent of an aging society, well-being trends have been deeply rooted in society as a whole. Thereby, interest in herbal medicines, which have been handed down as natural plant materials and traditional folk remedies in all fields such as foods, cosmetics, and residential environments, is increasing day by day.

Relatively, in the field of cosmetics industry, an attempt has been made to commercialize products manufactured by using natural plant materials as a raw material for a long time. In addition, in the field of functional food, preventive medicine and therapeutic medicine, oriental plant-based herbal medicines have begun to be approved and commercialized in the U.S and Europe, and accordingly, interest in the effectiveness of the natural plant materials and herbal medicines on the human body is increasing.

Natural plant materials contain various physiologically active substances and antioxidants, and thus, exhibit various effects such as anti-aging, anti-cancer, anti-inflammatory, and immune function-improving effects. However, they are unstable and sometimes irritating after extraction, and may be often toxic to the human body.

For these reasons, many studies have been recently conducted to improve the effects by stabilizing natural extracts, reducing toxicity, or converting the natural plant materials into a stable derivative.

As part of these studies, biological transformation methods using microorganisms or enzymes have been developed, a representative example of which is a fermentation process.

Fermentation is a process in which an organic substance is decomposed by using enzymes possessed by microorganisms to produce a material useful for the human body. In particular, representative fermentation microorganisms include *Monascus purpureus*, yeast or the like.

The fermentation allows, in addition to producing useful materials, *Monascus purpureus* involving in fermentation to play a role of immunity and detoxification in the intestines. Furthermore, the components ingested through fermentation by intestinal microorganisms are decomposed and converted into low-molecular materials that can be easily absorbed by human cells, or converted into active forms from unstable or inactive forms and absorbed. These results directly demonstrate the importance of the biological conversion by intestinal microorganisms.

Accordingly, attempts to maximize the efficacy of natural plant materials and herbal medicines by fermentation of microorganisms such as *Monascus purpureus*, yeast or the like, or to solve safety problems provide an important significance in product development in various fields of foods, cosmetics, drugs, and the like.

*Monascus* pigment produced by *Monascus purpureus* belonging to the genus of *Monascus* is used as a food additive, and many of research findings have been reported to verify the effectiveness of physiologically active substances such as monacolin K, mevinolin, lovastatin, γ-aminobutyric acid (GABA), acetylcholine and the like in the inhibition of cholesterol biosynthesis enzyme (HMG-CoA reductase) activity, inhibition of blood pressure elevation and antioxidant activity.

Due to the excellent physiological activity of red yeast rice, research on the development of novel health functional foods using the same has been actively conducted. As an example, miso, red pepper paste, fermented buckwheat, fermented soybeans and the like manufactured using red yeast rice as a raw material are being commercialized, and products, in which red yeast rice is applied to the cosmetics field, are also being developed.

PRIOR ART DOCUMENT

Patent Document

Korean Patent Registration No. 10-1709734 (published on Feb. 23, 2017)

DETAILED DESCRIPTION OF THE DISCLOSURE

Technical Problem

In view of the above, the present inventors have attempted to find out a method for further improving the skin-improving efficacy possessed by red yeast rice, and have discovered that an effective material having further improved skin-improving efficacy can be obtained by further fermenting red yeast rice with yeast, thereby completing the present disclosure.

Therefore, it is one object of the present disclosure to provide an external-use skin preparation composition capable of providing excellent antioxidant and anti-aging effects by containing an extract of a fermented product of red yeast rice.

Technical Solution

In order to achieve the object above, one aspect of the present disclosure provides an external-use skin preparation composition containing, as an active ingredient, an extract of a fermented product of red yeast rice, which is obtained by fermenting rice with *Monascus purpureus*, followed by further fermenting with yeast.

Another aspect of the present disclosure provides a method for improving skin elasticity or reducing skin wrinkles in a subject, including the step of locally applying an external-use skin preparation composition containing, as an active ingredient, an extract of a fermented product of red yeast rice to a subject in need of improvement of skin elasticity or reduction of skin wrinkles.

Advantageous Effects

The composition of the present disclosure contains an extract of a fermented product of red yeast rice and thereby, provide more excellent antioxidant and anti-aging effects compared to a conventional composition containing red yeast rice, while being safe.

DETAILED DESCRIPTION OF THE EMBODIMENTS

Figure 1:
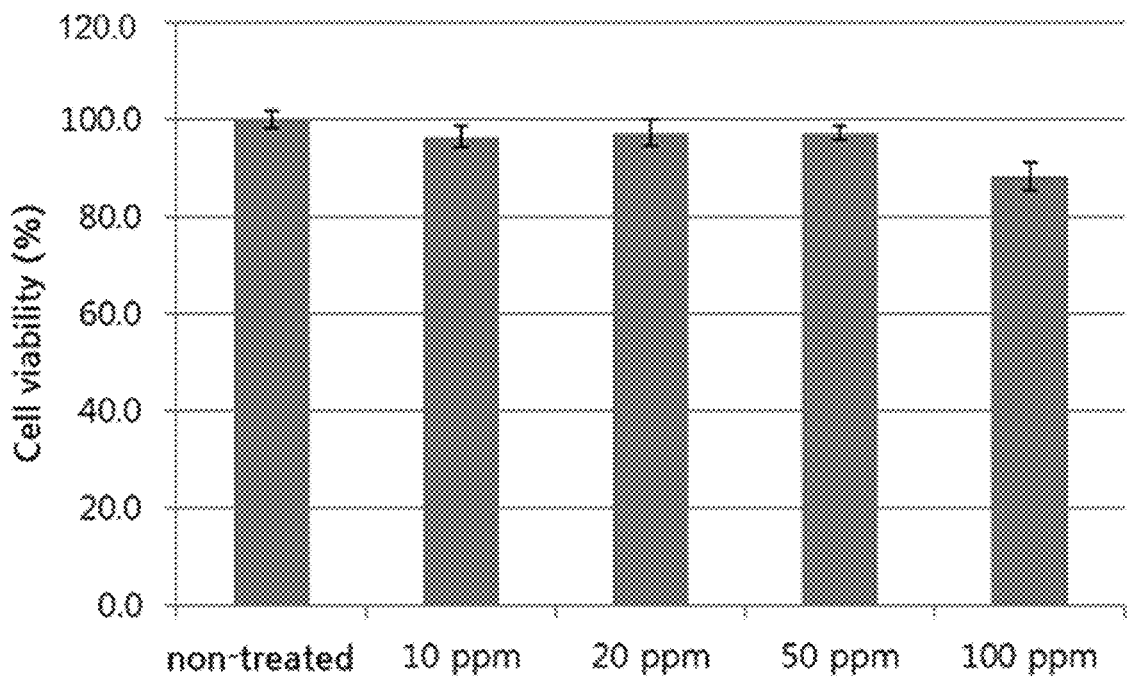
FIG. 1 is a graph showing the effect of the extract of the fermented product of red yeast rice according to the present disclosure on the growth of skin cells.

One aspect of the present disclosure provides an external-use skin preparation composition containing, as an active ingredient, an extract of a fermented product of red yeast rice, which is obtained by fermenting with *Monascus purpureus*, followed by further fermenting with yeast.

Another aspect of the present disclosure provides a method for improving skin elasticity or reducing skin wrinkles in a subject, including the step of locally applying an external-use skin preparation composition containing, as an active ingredient, an extract of a fermented product of red yeast rice to a subject in need of improvement of skin elasticity or reduction of skin wrinkles.

Red yeast rice is red rice produced by inoculating polished rice with the genus *Monascus* (e.g., *Monascus purpureus*) and fermenting for 5 to 30 days, preferably 15 to 30 days. In the fermentation process, the red natural pigment monacolin-K is produced, which contains gamma-aminobutyric acid (GABA) as a main component and exhibits effects including brain function activation, prevention of lifestyle diseases, promotion of brain development, cholesterol removal, amelioration and prevention of diabetes, blood pressure drop, and the like.

In one aspect of the present disclosure, a fermented product of red yeast rice is used, which can be produced by a process in which red yeast rice produced by inoculating and fermenting polished rice with *Monascus purpureus* is inoculated with yeast, and additionally fermented.

In one aspect of the present disclosure, as the yeast, *Saccharomyces* sp., *Schizosaccharomyces* sp., *Torulopsis* sp., *Rhodotorula* sp., *Candida* sp., or the like may be used, and preferably, *Saccharomyces* sp. may be used. Specifically, *Saccharomyces cerevisiae*, in particular, the *Saccharomyces cerevisiae* KCCM12008P strain (JTL-L1) may be used. *Saccharomyces cerevisiae* KCCM12008P strain (JTL-L1) is deposited at the Korean Culture Center of Microorganisms (KCCM) at Yurim B/D, 45, Hongjenae-4ga-gil, Seodaemun-gu, Seoul 120-861, Republic of Korea on Apr. 4, 2017 under the accession number KCCM12008P according to the Budapest Treaty on the International Recognition of the Deposit of Microorganisms For the Purposes of Patent Procedure.

The extract of the fermented product of red yeast rice used herein is intended to include not only an extract obtained from red yeast rice, which is completely fermented by sequentially inoculating polished rice with *Monascus pilosus* and yeast, but also a concentrate obtained by concentrating part or all of the extract, and an infusion, decoction, tincture and fluid extract obtained by drying the concentrate, as well as chemical substances contained in the red yeast rice fermented twice, which exhibit the main effects, and also the red yeast rice itself.

The extract of the fermented product of red yeast rice used herein can be prepared by any method known in the art. For example, the red yeast rice after fermentation is put in water or an organic solvent, extracted under reflux, deposited, then residue and a filtrate are separated through filter-cloth filtration and centrifugation, and the separated filtrate is concentrated under reduced pressure to obtain the red yeast rice extract. An organic solvent that may be used herein may be selected from ethanol, methanol, butanol, ether, ethyl acetate, chloroform, butylene glycol, and the like, and mixed solvents of these organic solvents and water. Herein, the extraction is preferably performed at a temperature of 15 to 45° C. for 5 to 48 hours. If the extraction temperature and time are out of the above ranges, the extraction efficiency may decrease, or a change in the components of the red yeast rice may occur. The extract obtained using the solvent as described above may be macerated, heated and filtered according to a conventional method known in the art to obtain a liquid material. Alternatively, the solvent may be further evaporated, followed by spray-drying or freeze-drying.

The external-use skin preparation composition according to the present disclosure may contain the extract of the fermented product of red yeast rice in an amount of 0.01 to 10% by weight, based on the total weight of the composition. If the content of the extract is less than 0.01% by weight, the efficacy and effect of the extract may be insignificant, and if the content is more than 10% by weight, it may negatively affect the fragrance and feeling of use of the composition.

The composition according to the present disclosure may be used as an antioxidant or anti-aging external-use skin preparation composition, and may be particularly used as a composition for improving skin elasticity or reducing skin wrinkles.

The composition according to the present disclosure suppresses skin damage caused by oxidation or ultraviolet rays, and promotes collagen production, reducing skin wrinkles and improving skin elasticity, and thereby provides an effect in suppressing skin aging.

The composition according to the present disclosure may be formulated as a cosmetic composition or a pharmaceutical composition, but is not limited thereto.

The composition according to the present disclosure may be formulated by containing a cosmetically and dermatologically acceptable medium or base. The composition may be provided in any form suitable for topical application, for example, in the form of solutions, gels, solids, paste anhydrous products, emulsions obtained by dispersing oil phase in aqueous phase, suspensions, microemulsions, microcapsules, microgranules or ionic (liposomes) and non-ionic vesicle dispersants, or in the form of creams, skins, lotions, powders, ointments, sprays or conceal stick. It may also be used in the form of a foam or an aerosol composition further containing a compressed propellant.

These compositions may be prepared in accordance with a conventional method in the art.

In addition, the composition according to the present disclosure may contain adjuvants commonly used in cosmetic or dermatological fields such as fatty materials, organic solvents, solubilizing agents, thickening agents, gelling agents, softening agents, antioxidants, suspending agents, stabilizing agents, foaming agents, flavoring agents, surfactants, water, ionic or non-ionic emulsifiers, fillers, sequestering agents, chelating agents, preservatives, vitamins, blockers, wetting agents, essential oils, dyes, pigments, hydrophilic or lipophilic active agents, lipid vesicles or any other ingredient commonly used in cosmetics. Such adjuvants are introduced in the amounts commonly used in the cosmetic or dermatological fields.

Further, the composition according to the present disclosure may further contain a skin absorption-promoting material in order to increase the skin-improving effect.

Hereinafter, the composition and effect of the present disclosure will be described in more detail by way of Examples and Test Examples. However, these Examples and Test Examples are given for illustrative purposes only to help understanding of the present disclosure, and the scope of the present disclosure is not limited by these examples.

[Example 1] Preparation of Extract of Fermented Product of Red Yeast Rice (JTL-L1)

1) Preparation of Red Yeast Rice

In order to prepare red yeast rice, *Monascus purpureus* (KCTC 6120) was used as a strain. Polished rice was soaked in water at a weight ratio of 1:1 for 1 hour and then sterilized by heating. The *Monascus purpureus* strain (10 CFU/ml) was inoculated into 100 g of the sterilized polished rice and subjected to stationary culture under aerobic conditions at 30° C. for 2 days and at 25° C. for 6 days. After completion of the fermentation, the red yeast rice was heated at 90° C. for 1 hour to kill the *Monascus purpureus*.

2) Preparation of Fermented Product of Red Yeast Rice using Yeast

A 2-fold weight of distilled water was added to the sterilized red yeast rice, and the rice was inoculated with yeast. As the yeast, the *Saccharomyces cerevisiae* (JTL-L1, KCCM12008P) strain was used, and the rice was further fermented aerobically at 25 to 30° C. for 7 days after inoculation.

3) Preparation of Extract of Fermented Product of Red Yeast Rice

After the yeast fermentation was completed, the red yeast rice was removed through centrifugation, and the remaining supernatant was concentrated under reduced pressure to be ⅒ of the initial volume. Subsequently, 4-fold volume of 95% ethanol was slowly added to the concentrated solution, and the mixture was allowed to stand at 4° C. for 24 hours to carry out a precipitation reaction using ethanol. Thereafter, the supernatant was removed through centrifugation, and the precipitated extract was freeze-dried and used in the experiment.

[Comparative Example 1] Preparation of Red Yeast Rice Extract

In order to prepare red yeast rice, *Monascus purpureus* (KCTC 6120) was used as a strain. Polished rice was soaked in water at a weight ratio of 1:1 for 1 hour and sterilized by heating. The *Monascus purpureus* strain (10 CFU/ml) was inoculated into 100 g of the sterilized polished rice and subjected to stationary culture under aerobic conditions at 30° C. for 2 days and at 25° C. for 6 days. Subsequently, the rice was heated at 90° C. for 20 minutes, and then dried at 50° C. to a water content of 10% or less. Then, the dried rice was ground with a grinder (food mixer FM-707T, Hanil, Seoul, Korea) to prepare red yeast rice powder.

A 5-fold volume of 80% ethanol was added to the prepared red yeast rice powder, which was then extracted for 3 hours at room temperature. Thereafter, the red yeast rice that had been subsided through centrifugation was discarded, and the supernatant was concentrated under reduced pressure to remove ethanol, dried, and then used in the experiment.

[Comparative Example 2] Preparation of Extract of Fermented Product of Red Yeast Rice Yeast (KCTC7296)

An extract of a fermented product of red yeast rice yeast (KCTC7296) was prepared in the same manner as in Example 1, except that the *Saccharomyces cerevisiae* (KCTC7296) strain was used as yeast.

[Comparative Example 3] Preparation of Extract of Fermented Product of Red Yeast Rice Yeast (KCTC17715)

An extract of a fermented product of red yeast rice yeast (KCTC17715) was prepared in the same manner as in Example 1, except that the *Saccharomyces cerevisiae* (KCTC17715) strain was used as yeast.

[Test Example 1] Evaluation of Cytotoxicity

In order to determine cytotoxicity of the extracts of fermented product of red yeast rice, human keratinocyte cell line (purchased from Invitrogen) was treated with the extracts with varying concentrations, and the viability of the cells was measured.

The human keratinocyte cell line was seeded in a 96-well plate at a concentration of $1.0 \times 10^4$ cells/well and cultured overnight. The cells were treated with varying concentrations (10, 20, 50, 100 ppm) of the extract of the fermented product of red yeast rice of Example 1 and cultured again for 24 hours. For comparison, the cells were cultured for 24 hours without treatment with the extract of the fermented product of red yeast rice. After culture, the medium was removed, and the cells were washed with PBS, after which 0.1 mg/ml MTT (thiazolyl blue tetrazolium blue, Sigma) solution was added to the cells, and then, the cells were cultured at 37° C. for 2 hours. Thereafter, the added MTT solution was removed, and the purple precipitate was dissolved in an organic solvent DMSO (dimethyl sulfoxide, Sigma Aldrich). Then, the absorbance of the solution at a wavelength of 570 nm was measured using a Synergy 2 spectrophotometer (BioTek), and the effect of the extract on the proliferation of the cells was evaluated. The results of the measurement are shown in FIG. 1.

As shown in FIG. 1, it was found that the extract of the fermented product of red yeast rice according to the present disclosure showed no effect on the growth of keratinocytes until the concentration of 100 ppm.

[Test Example 2] Evaluation of Antioxidant Effect

The antioxidant effect was evaluated in human keratinocyte cell line (HaCaT) using the DCF-da measurement method. The human keratinocyte cell line was seeded by 100 µl in a 96-well plate at a concentration of $2.0 \times 10^5$ cells/mL and cultured for 24 hours. Then, the cells were treated with the extract of the fermented product of red yeast rice of Example 1, the red yeast rice extract of Comparative Example 1, and the extract of the fermented product of red yeast rice obtained using different strains of yeasts of Comparative Examples 2 and 3 at a concentration of 50 ppm. As a positive control, the cells were treated with L-ascorbic acid at a concentration of 200 µg/mL, and then further cultured for 3 hours. The samples and media were washed with the Hank's balanced salt solution (HBSS) buffer and treated with the 2,7-dichlorodihydrofluorescein diacetate (DCF-da) solution at a concentration of 50 µM. The light was blocked for 20 minutes and allowed to react at 37° C., and the DCF-da solution was washed again using the HBSS buffer. The initial fluorescence value was measured using a photometer (PERKIN ELMER, 1420-VICTOR2™), and then, UVB was irradiated at 20 mJ/cm$^2$. After 2 hours, the fluorescence value was measured again to compare the increase in the fluorescence values.

Figure 2:
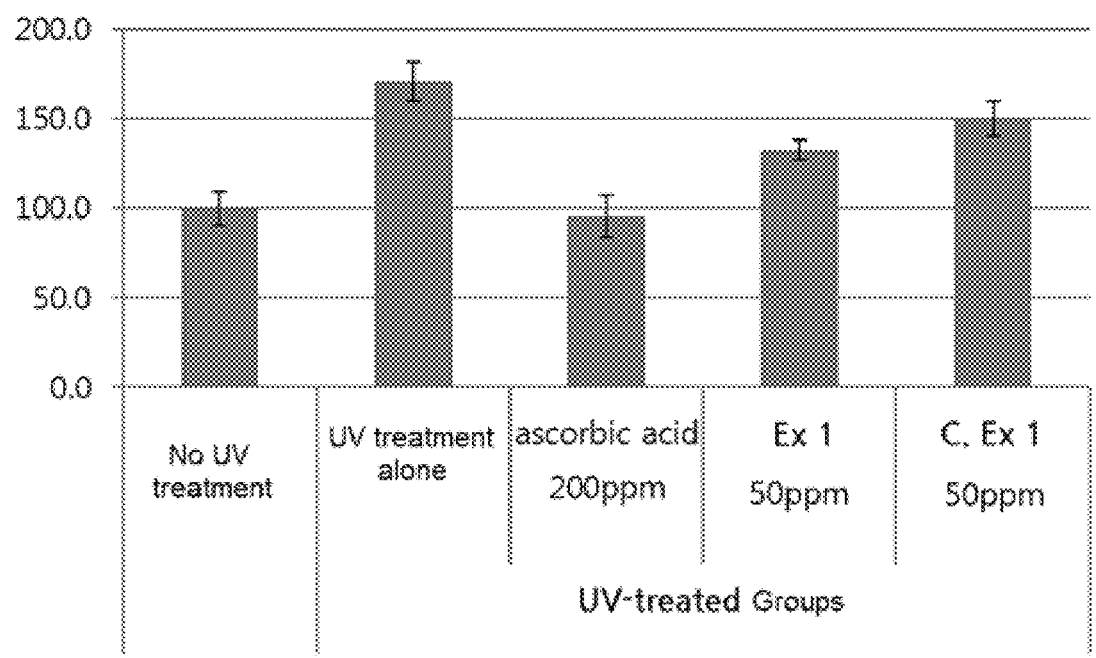
FIG. 2 is a graph showing the antioxidant effect of the extract of the fermented product of red yeast rice according to the present disclosure on skin cells.
Figure 3:
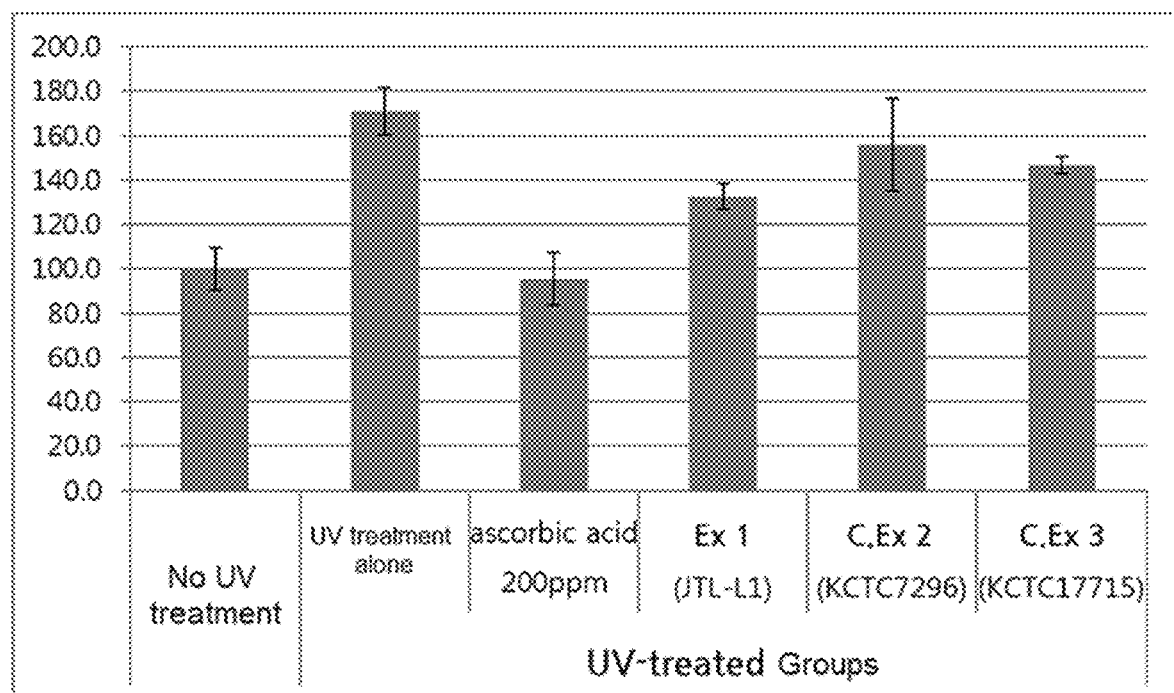
FIG. 3 is a graph showing the antioxidant effect of the extract of the fermented product of red yeast rice using the yeast according to the present disclosure and the extract of the fermented product of red yeast rice further fermented with other bacteria on skin cells.

The results of the measurement are shown in FIGS. 2 and 3.

FIG. 2 shows the antioxidant effect exhibited by the cells treated with the extract of the fermented product of red yeast rice of Example 1, the red yeast rice extract of Comparative Example 1 and ascorbic acid, and it can be confirmed therefrom that the extract of the fermented product of red yeast rice according to the present disclosure exhibited more superior antioxidant effect than the red yeast rice extract.

FIG. 3 shows the antioxidant effect exhibited by the cells treated with the extracts of the fermented product of red yeast rice of Example 1, Comparative Examples 2 and 3, and ascorbic acid, and it can be confirmed therefrom that when the cells were treated with the extracts of the fermented product of red yeast rice of Comparative examples 2 and 3, which were obtained using different species of yeasts, the cells exhibited antioxidant effect similar to that of the red yeast rice extract of Comparative example 1. In contrast, when the cells were treated with the extract of the fermented product of red yeast rice according to the present disclosure, the cells exhibited more superior antioxidant effect, and it can be also confirmed that even when the fermented products of red yeast rice were obtained using different yeast species, there was a difference in efficacy of the fermented products obtained according to different yeast species.

[Test Example 3] Induction of Type 1 Collagen Production

The anti-aging effect was evaluated by the degree of induction of type 1 collagen production. Human skin cell line (adult normal human dermal fibroblast CC-2511, Lonza) was seeded in a 12-well plate at a concentration of $10^5$ cells/well and cultured for 24 hours. Subsequently, the cells were treated with the extract of the fermented product of red yeast rice of Example 1 at concentrations of 50 ppm and 100 ppm, and further cultured for 24 hours. Total RNA was extracted from the fibroblasts, and RT-PCR (the cells were treated at 95° C. for 20 seconds, 95° C. for 3 seconds and 60° C. at 30 seconds, and this process was repeated for a total of 40 cycles) was performed to compare the degree of gene expression of collagen type I alpha 1 chain (colla1). The primer sequences for the colla1 gene used herein were as follows:

Forward primer: 5'-GTC ACC CAC CGA CCA AGA AAC C-3' (SEQ ID NO: 1)
Reverse primer: 5'-AAG TCC AGG CTG TCC AGG GAT G-3' (SEQ ID NO: 2).

Figure 4:
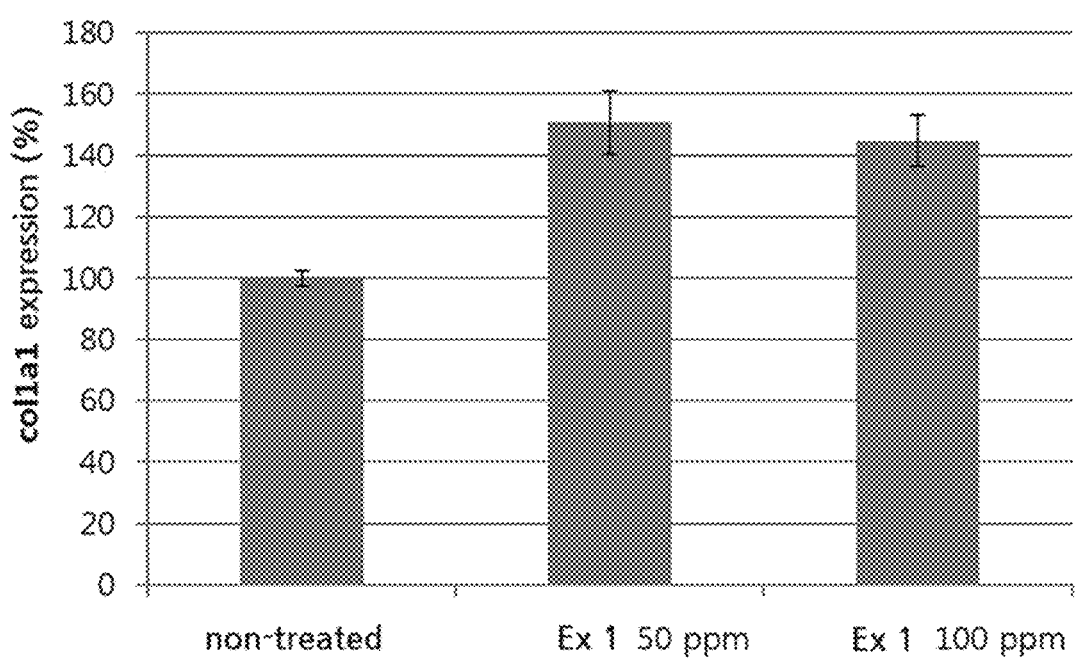
FIG. 4 is a graph showing the effect of the extract of the fermented product of red yeast rice according to the present disclosure on the expression of collagen type I alpha 1 chain (colla1).

The results of the measurement are shown in FIG. 4.

Referring to FIG. 4, it can be confirmed that when the cells were treated with the extract of the fermented product of red yeast rice according to the present disclosure, the cells appeared to increase the expression of colla1, and it helps to reduce skin wrinkles and improve skin elasticity by promoting collagen production, and can ultimately exert anti-aging effects.

The invention claimed is:

1. A method for improving skin elasticity of a subject in need thereof, comprising applying an topical skin preparation composition containing, as an active ingredient, an extract of a fermented product of Red yeast rice to skin of the subject,
   wherein the fermented product of Red yeast rice is a fermentation product obtained by fermenting rice with a *Monascus purpureus* strain, followed by further fermenting with a *Saccharomyces cerevisiae* strain, and
   wherein the *Saccharomyces cerevisiae* strain is a *Saccharomyces cerevisiae* JTL-L1 strain deposited under accession number KCCM (Korean Culture Center of Microorganisms) 12008P.

2. A method for reducing skin wrinkles in a subject in need thereof, including applying a topical skin preparation composition containing, as an active ingredient, an extract of a fermented product of Red yeast rice to skin of the subject,
   wherein the fermented product of Red yeast rice is a fermentation product obtained by fermenting rice with a *Monascus purpureus* strain, followed by further fermenting with a *Saccharomyces cerevisiae* strain, and
   wherein the *Saccharomyces cerevisiae* strain is a *Saccharomyces cerevisiae* JTL-L1 strain deposited under accession number KCCM (Korean Culture Center of Microorganisms) 12008P.

3. The method of claim 1, wherein the extract is contained in an amount of 0.01 to 10% by weight based on the total weight of the composition.

4. The method of claim 1, wherein the extract is prepared using ethanol as an extraction solvent.

5. The method of claim 1, wherein the composition is a cosmetic composition.

6. The method of claim 2, wherein the extract is contained in an amount of 0.01 to 10% by weight based on the total weight of the composition.

7. The method of claim 2, wherein the extract is prepared using ethanol as an extraction solvent.

8. The method of claim 2, wherein the composition is a cosmetic composition.

* * * * *